(12) United States Patent
Kelly et al.

(10) Patent No.: US 8,738,134 B2
(45) Date of Patent: May 27, 2014

(54) HANDLING IMPROPER DEVICE DATA IN IMPLANTABLE DEVICES

(71) Applicant: Cardiac Pacemakers, Inc., St. Paul, MN (US)

(72) Inventors: Jonathan H. Kelly, Woodbury, MN (US); Gang Wu, San Clemente, CA (US); James Kalgren, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/761,653

(22) Filed: Feb. 7, 2013

(65) Prior Publication Data

US 2013/0150914 A1 Jun. 13, 2013

Related U.S. Application Data

(63) Continuation of application No. 12/273,708, filed on Nov. 19, 2008, now Pat. No. 8,374,694.

(60) Provisional application No. 61/017,691, filed on Dec. 30, 2007.

(51) Int. Cl.
*A61N 1/00* (2006.01)

(52) U.S. Cl.
USPC .................................. 607/30; 607/31; 607/60

(58) Field of Classification Search
USPC ................................................ 607/30–31, 60
See application file for complete search history.

(56) References Cited

U.S. PATENT DOCUMENTS

| | | | |
|---|---|---|---|
| 6,823,210 B2 | 11/2004 | Eberle et al. | |
| 7,383,088 B2 | 6/2008 | Spinelli et al. | |
| 7,840,268 B2 | 11/2010 | Blischak et al. | |
| 2004/0088020 A1 | 5/2004 | Condie et al. | |
| 2005/0256550 A1 | 11/2005 | Gilkerson et al. | |
| 2009/0171412 A1 | 7/2009 | Kelly et al. | |

OTHER PUBLICATIONS

"U.S. Appl. No. 12/273,708, Response filed Feb. 21, 2012 to Final Office Action mailed Nov. 18, 2011", 10 pgs.
"U.S. Appl. No. 12/273,708, Response filed Aug. 23, 2011 to Non Final Office Action mailed May 24, 2011", 12 pgs.
"U.S. Appl. No. 12/273,708, Examiner Interview Summary mailed Jan. 30, 2012", 3 pgs.
"U.S. Appl. No. 12/273,708, Final Office Action mailed Nov. 18, 2011", 8 pgs.
"U.S. Appl. No. 12/273,708, Non Final Office Action mailed May 24, 2011", 8 pgs.
"U.S. Appl. No. 12/273,708, Notice of Allowance mailed Oct. 11, 2012", 7 pgs.

*Primary Examiner* — Nicole F Lavert
(74) *Attorney, Agent, or Firm* — Schwegman Lundberg & Woessner, P.A.

(57) ABSTRACT

A system and method for handling data received from an implantable medical device (IMD) is provided. The method includes communicating a device parameter value of an IMD device parameter from the IMD to an external device and determining, at the external device, that the communicated device parameter value is at an improper value. Additionally, in response to the determining that the communicated device parameter value is at an improper value, automatically performing at least one of re-programming the IMD device parameter with a selected substitute device parameter value, ignoring, or purging non-programmable data.

21 Claims, 4 Drawing Sheets

HANDLING IMPROPER DEVICE DATA IN IMPLANTABLE DEVICES

CLAIM OF PRIORITY

This application is a continuation of and claims the benefit of priority under 35 U.S.C. §120 to U.S. patent application Ser. No. 12/273,708, filed on Nov. 19, 2008, now issued as U.S. Pat. No. 8,374,694, which claims the benefit of priority under 35 U.S.C. §119(e) of U.S. Provisional Patent Application Ser. No. 61/017,691, filed on Dec. 30, 2007, the benefit of priority of each of which is claimed hereby, and each of which are incorporated by reference herein in its entirety.

TECHNICAL FIELD

This document pertains generally to implantable devices, and more particularly, but not by way of limitation, to handling of device data in implantable medical devices.

BACKGROUND

Implantable medical devices (IMDs) can be implanted into patients for various purposes, such as heart rhythm management and stimulation. Some examples of these devices include cardiac function management (CFM) or cardiac rhythm management (CRM) devices such as implantable pacemakers, implantable cardioverter defibrillators (ICDs), cardiac resynchronization devices, and devices that include a combination of such capabilities. CFM IMDs, for example, can monitor for cardiac arrhythmia, and administer therapy in response.

IMDs can communicate wirelessly with an external device. Examples of the external device can include an IMD programmer that provides bi-directional communication between the IMD and the caregiver, a patient activator that calls a patient to activate an implantable device, or a patient data display that reads and displays information from the IMD.

OVERVIEW

The present inventors have recognized, among other things, that in a cardiac rhythm management system (CRM), handling of unexpected values (such as for example, therapeutic settings of the IMD) can be challenging. Such unexpected values may be generated at the IMD, for example, due to alpha particle radiation, which can flip memory bits, thereby corrupting such therapeutic settings or other data stored in the memory.

This document describes a strategy for handling unexpected or corrupted IMD data in an associated external device. Such improper device data can be handled so as to provide a consistent and safe state for the implantable medical device or the associated external device.

Example 1 describes a system. In this example, the system comprises an implantable medical device (IMD) implanted in a patient. In this example, the system also comprises an external device in communication with the IMD and configured to receive a device parameter value of an IMD device parameter from the IMD to an external device, to determine that the communicated device parameter value is at an improper value, to automatically perform at least one of: re-program the IMD device parameter with a selected substitute device parameter value, and to ignore or purge non-programmable data.

In Example 2, the system of Example 1 optionally comprises the external device being configured to compare the communicated device parameter value against an allowable range or list of values for the device parameter.

In Example 3, the system of one or more of Example 1-2 is optionally configured to determine that a plurality of values of respective device parameters communicated from the IMD violates a rule constraining a combination of allowable values of the respective device parameters.

In Example 4, the system of one or more of Examples 1-3 is optionally configured to re-program at least one of the plurality of values of respective device parameters upon determining that the plurality of values of respective device parameters violates the rule constraining the combination of allowable values of the respective device parameters.

In Example 5, the system of one or more of Examples 1-4 is optionally configured to re-program the IMD device parameter to a nominal value specified for the IMD.

In Example 6, the system of one or more of Examples 1-5 is optionally configured to re-program the IMD device parameter to a nominal value that is based on an indication manifested by the patient.

In Example 7, the system of one or more of Examples 1-6 is optionally configured to purge non-programmable data associated with the improper value of the IMD device parameter.

In Example 8, the system of one or more of Examples 1-7 is optionally configured to automatically re-program the IMD device parameter with a selected substitute device parameter value in response to determining that the communicated device parameter value is at an improper value.

In Example 9, the system of one or more of Examples 1-8 is optionally configured to automatically purge non-programmable data in response to determining that the communicated device parameter value is at an improper value.

In Example 10, the system of one or more of Examples 1-9 is optionally configured to purge non-programmable physiological data communicated from the IMD to the external device in response to the determining that the communicated device parameter value is at an improper value.

Example 11 describes a method of handling data received from an implantable medical device (IMD) for a patient, the method comprising: communicating a device parameter value of an IMD device parameter from the IMD to an external device; determining, at the external device, that the communicated device parameter value is at an improper value; in response to the determining that the communicated device parameter value is at an improper value, automatically performing at least one of: re-programming the IMD device parameter with a selected substitute device parameter value; and ignoring or purging non-programmable data.

In Example 12, the method of Example 11 is optionally performed such that the determining that the communicated device parameter value is at an improper value includes comparing the communicated device parameter value against an allowable range or list of values for the device parameter.

In Example 13, the method of any one or more of Examples 11-12 is optionally performed such that the determining that the communicated device parameter value is at an improper value includes determining that a plurality of values of respective device parameters communicated from the IMD violates a rule constraining a combination of allowable values of the respective device parameters.

In Example 14, the method of any one or more of Examples 11-13 is optionally performed to include re-programming at least one of the plurality of values of respective device parameters upon determination that the plurality of values of respective device parameters violates the rule constraining the combination of allowable values of the respective device parameters.

In Example 15, the method of any one or more of Examples 11-14 is optionally performed such that the re-programming the IMD device parameter comprises re-programming to a nominal value specified for the IMD.

In Example 16, the method of any one or more of Examples 11-15 is optionally performed such that the re-programming the IMD device parameter comprises re-programming to a nominal value that is based on an indication manifested by the patient.

In Example 17, the method of any one or more of Examples 11-16 is optionally performed such that the purging non-programmable data comprises purging physiological data associated with the improper value of the IMD device parameter.

In Example 18, the method of any one or more of Examples 11-17 is optionally performed such that in response to the determining that the communicated device parameter value is at an improper value, automatically re-programming the IMD device parameter with a selected substitute device parameter value.

In Example 19, the method of any one or more of Examples 11-18 is optionally performed such that in response to the determining that the communicated device parameter value is at an improper value, automatically purging non-programmable data.

In Example 20, the method of any one or more of Examples 11-19 is optionally performed such that in response to the purging non-programmable data comprises purging physiological episode data communicated from the IMD to the external device.

In Example 21, the method of any one or more of Examples 11-20 is optionally performed such that the re-programming the IMD device parameter comprises re-programming at least one of a therapy parameter or a sensing parameter.

In Example 22, the method of any one or more of Examples 11-21 is optionally performed such that the re-programming a therapy parameter includes re-programming a bradycardia mode parameter, a tachycardia mode parameter, pacing rate parameter.

In Example 23, the method of any one or more of Examples 11-22 is optionally performed such that the re-programming a sensing parameter includes re-programming at least one of a sensing configuration parameter.

In Example 24, the method of any one or more of Examples 11-23 is optionally performed such that the purging non-programmable data comprises purging at least one of episode identification data, episode detail data, episode therapy data, electro-gram data, episode marker data or a trended data.

In Example 25, the method of any one or more of Examples 11-24 is optionally performed such that the purging trended data includes purging at least one of heart rate data, activity level data, fault data, pace count data, sense count data or therapy count data.

In Example 26, the method of any one or more of Examples 11-25 is optionally performed to comprise communicating an alert to a user upon determining, at the external device, that the communicated device parameter is at an improper value.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

An implantable medical device (IMD) generally refers to any medical device that can be implanted in a patient. By way of example, but not limitation, an IMD may be operable to sense a physiologic parameter, such as blood pressure, temperature, posture, blood sugar levels, or others. Some IMDs, such as implantable cardioverter-defibrillators (ICDs) and pacemakers (PMs), store electrogram (EGM) data. An IMD may be operable to provide therapy, such as, but not limited to, pulses for rhythm management in a patient's heart. An IMD may provide other functions, such as communication. For example, IMDs can transmit stored data to external devices, such as an IMD programmer (PRM) or an in-home monitoring device.

The present inventors have recognized, among other things, an efficient strategy for handling of improper device data transmitted by an implantable medical device.

Figure 1A:
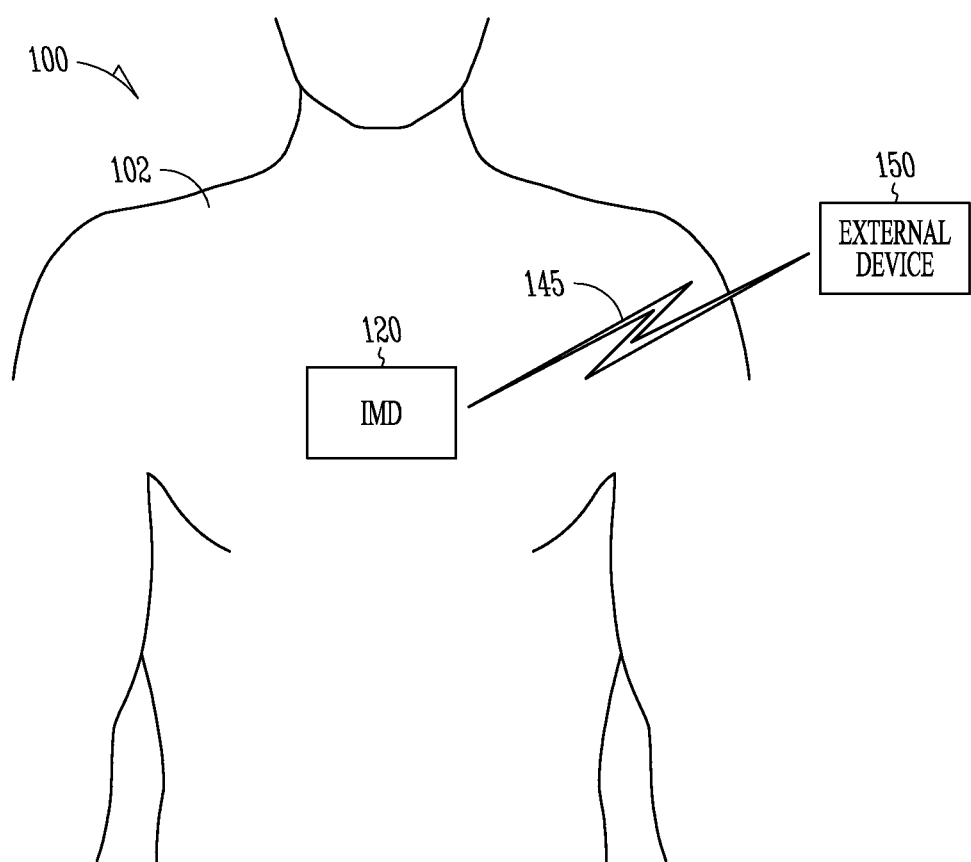
FIG. 1A is an illustration of an example of an implantable device and an external device.

FIG. 1A shows an example of a system 100 including an implantable medical device 120 in a body 102 in communication with an external device 150. In an example, the external device 150 is configured to receive a number of device parameter values from the implantable medical device 120. Device parameter data can include either programmable data (user configurable) or read-only data. In an example, programmable data can be read from the IMD during initial interrogation. In an example, read-only data that can be read during initial interrogation and background interrogation. In an example, device parameter data can include various values related to calibration, algorithm control, device configuration, or the like. In certain examples, such device parameters can include one or more counter values, such as related to occurrences of atrial tachycardia, ventricular tachycardia, atrial bradycardia, ventricular bradycardia, or the like. In an example, the device parameter data can include histograms that are related to atrial arrhythmia, ventricular arrhythmia, atrial pacing, ventricular pacing, or the like. In an example, the device parameter data can include trended data that are related to respiratory rate, patient activity, heart rate variability, or the like. In an example, the device parameter data can include fault information data related to any faults detected in the implantable medical device 120. In an example, the device parameter data can include magnet data which can include data parameters to configure the device behavior upon application of a magnetic field on the IMD. In some examples, magnet data parameter can be configured to initiate or withhold therapy when a magnetic field is applied on the IMD. In an example, the device parameter data can include device firmware revision information. In an example, the device parameters can include atrial or ventricular detection or therapy parameters. In an example, the device parameters can include various bradycardia or tachycardia parameters (such as pacing rate limit parameters, Atrial-to-Ventricular delay parameters, sensing configuration parameters, pacing configuration parameters, tachycardia detection parameters, therapy parameters, etc.). In an example, the device parameter can include device mode information, battery status information, intrinsic amplitude measurements or alerts, lead impedance measurements, information about the implantable medical device's internal clock(s), encrypted patient identification data, change logs (e.g., for atrial or ventricular tachycardia or bradycardia modes), or the like. In an example, device parameters can include episode summary (such as event ID, type, therapy summary, etc.), episode detail (such as event ID, type, detection and therapy details, etc.), EGM data, device marker data etc.

In an example, the external device 150 can be configured to determine that the communicated device parameter value is at an improper value. In a further example, the external device 150 can be configured to automatically re-program the IMD device parameter with a selected substitute device parameter value upon determining that the communicated device parameter value is at an improper value. In another further example, the external device 150 can be configured to ignore or purge non-programmable data upon determining that the communicated device parameter value is at an improper value.

In yet another example, external device 150 can be configured to determine that a device parameter value is at an improper value when plurality of values of respective device parameters communicated from the IMD violates a rule constraining a combination of allowable values of the respective device parameters. In an example, if at least one of the device parameters in a set of device parameters is determined to have an improper parameter value, then the parameter values for all of the device parameters within the set are re-programmed with selected substitute parameter values. In an example, the external device 150 is configured to re-program an improper device parameter to a nominal value that is based on an indication manifested by the patient. In an example, the selected substitute parameter value used for re-programming can be a nominal parameter value that is determined based upon a therapy provided for the patient. In another example, if at least one of the device parameters chosen from a set of device parameters is found to have an improper parameter value, then the parameter values for all of the device parameters within the set are ignored.

In an example, the external device 150 is configured to ignore or purge non-programmable physiological data communicated from the IMD 120 to the external device 150 in response to determining that a communicated device parameter value is at an improper value.

Figure 1B:
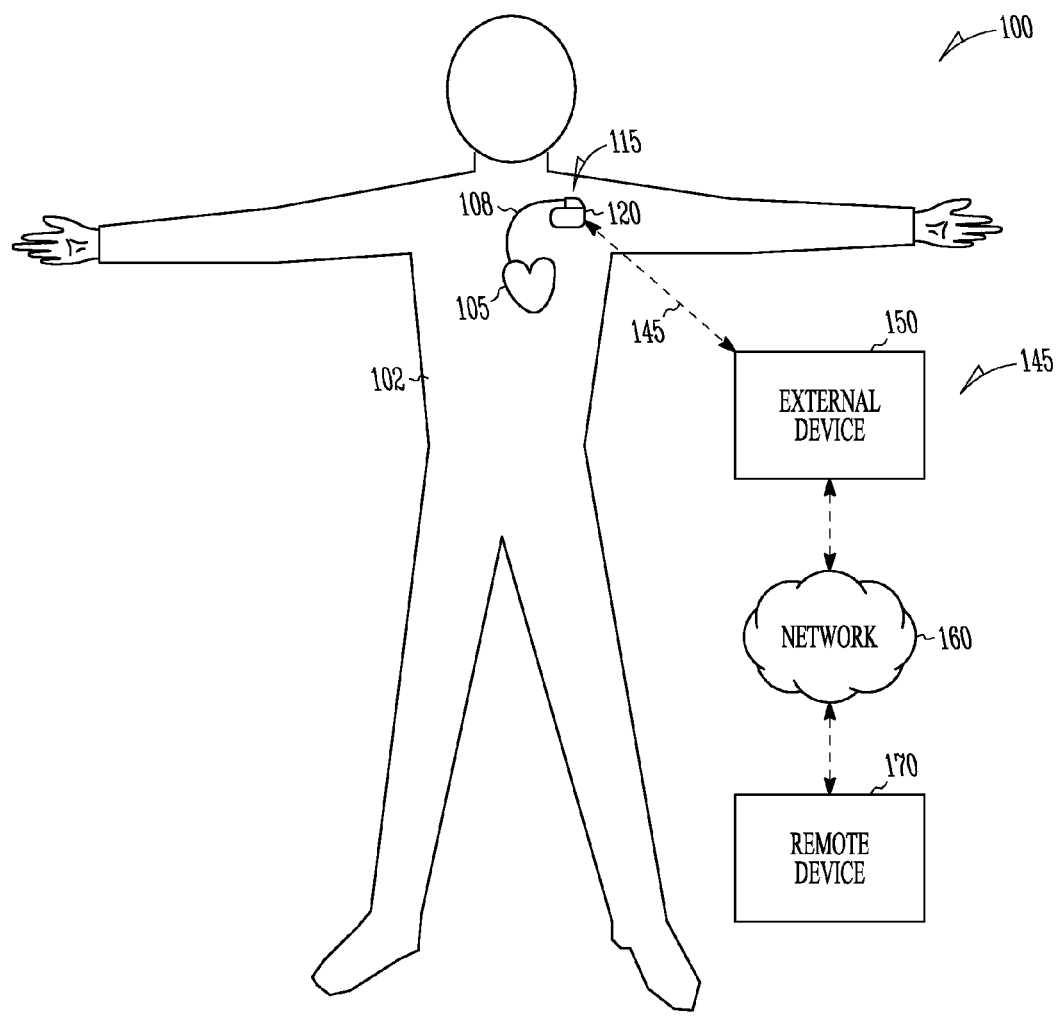
FIG. 1B is an illustration of an example of a CRM system, including an implantable medical device and an external system, and portions of an environment in which it is used.

FIG. 1B illustrates an example of portions of a CRM system 100 and portions of the environment in which the system 100 is used. In this example, the CRM system 100 includes an implantable system 115, an external system 155, and a telemetry link 145 providing bidirectional communication between the implantable system 115 and the external system 155. The implantable system 115 can include an implantable medical device 120 and a lead system 108. The implantable medical device 120 can be implanted within a body 102 and coupled to a heart 105, such as via the lead system 108. Examples of the implantable medical device 120 can include, but are not limited to, pacemakers, pacemaker/defibrillators, cardiac resynchronization devices, cardiac remodeling control devices, or cardiac monitors. In certain examples, the lead system 108 can include multiple leads, such as atrial or ventricular leads. In an example, the external system 155 can include a programmer. In another example, external system 155 can include a patient management system, which can include an external device 150 in proximity of implantable device 140, a remote device 170 that can be in a relatively distant location, and a telecommunication or other network 160 linking the external device 150 and the remote device 170. The patient management system can permit access to the implantable system 115 from a remote location, such as for monitoring patient status or adjusting one or more therapies. In certain examples, the telemetry link 145 can include an inductive telemetry link. In certain examples, the telemetry link 145 can include a far-field radio-frequency telemetry link. In an example, the telemetry link 145 provides data transmission from the implantable medical device 120 to the external system 155. This can include, for example, transmitting real-time physiological data acquired by the implantable medical device 120, extracting physiological data acquired by and stored in the implantable medical device 120, extracting therapy history data stored in the implantable medical device 120, or extracting data indicating an operational status of the implantable medical device 120 (e.g., battery status or lead impedance). In certain examples, the telemetry link 145 provides data transmission from the external system 155 to the implantable medical device 120. This can include, for example, programming the implantable medical device 120 to acquire physiological data, programming the implantable medical device 120 to perform at least one self-diagnostic test (such as for a device operational status), or programming the implantable medical device 120 to deliver at least one therapy. In an example, the external device 150 can be configured to receive various values of device parameters (such as described above) that can be transmitted by the implantable medical device 120.

Figure 2:
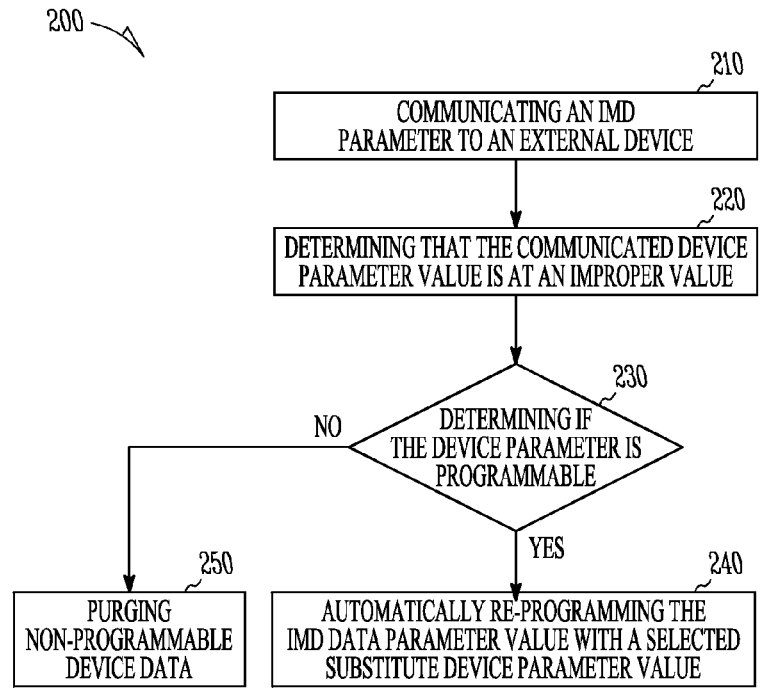
FIG. 2 illustrates an example of a method for handling data received from an implantable medical device (IMD) for a patient.

FIG. 2 illustrates an example of a method 200 for handling data received from an implantable medical device (IMD).

At 210, an IMD parameter is communicated to an external device. In an example, the telemetry link 145 provides data transmission from the implantable medical device 120 to the external device 150.

At 220, the method 200 includes determining whether the communicated device parameter value is at an improper value. In an example, if a communicated device parameter value is at an improper value, an alert is generated and provided to a user.

At 230, method 200 includes determining if the device parameter value is programmable or non-programmable after determining at 220 that the communicated device parameter value is at an improper value.

At 240, the improper IMD data parameter value automatically re-programmed with a selected substitute device parameter value. This can include over-writing the improper value with the selected substitute device parameter value in a memory of the IMD providing read-write access. In an example, upon automatically re-programming one or more IMD parameter values, the method 200 includes alerting a user about the re-programming event, which can include also providing the user with the one or more substitute device parameter values used for re-programming. In an example, alerting the care-giver or other user includes sending an alert signal from a local external device 150 to a remote patient care system 170.

In an example, re-programming includes re-programming at least one of a plurality of values of respective device parameters upon determining that the plurality of values of respective device parameters violates a rule constraining the combination of allowable values of the respective device parameters. In an example, re-programming the IMD device parameter includes re-programming to a nominal value specified for the IMD. In an example, re-programming the IMD device parameter includes re-programming to a nominal value that is based on an indication manifested by the patient. In an example, re-programming the IMD device parameter includes re-programming at least one of a therapy parameter or a sensing parameter. In an example, re-programming a therapy parameter includes re-programming a bradycardia mode parameter, a tachycardia mode parameter, or a pacing rate parameter. In an example, re-programming a sensing parameter includes re-programming a sensing configuration parameter.

At 250, method 200 includes ignoring or purging non-programmable data if an improper parameter value is detected. In an example, ignoring non-programmable data having improper values includes not acting on non-programmable data. In an example, purging non-programmable data includes deleting the data. In an example, ignoring or purging non-programmable data includes automatically ignoring or purging physiological data associated with an improper value of the IMD device parameter. In an example, ignoring or purging non-programmable data includes ignoring or purging physiological episode data communicated from the IMD 120 to the external device 150. In an example, ignoring or purging non-programmable data includes ignoring or purging at least one of episode identification data, episode detail data, episode therapy data, electro-gram data, episode marker data, or trended data. In an example, ignoring or purging trended data includes ignoring or purging at least one of heart rate data, activity level data, fault data, pace count data, sense count data, or therapy count data. In an example, ignoring or purging non-programmable data includes preventing physiological episode data from being displayed at the external device 150. In an example, purging non-programmable data includes deleting physiological episode data having improper values from the implantable medical device.

Figure 3:
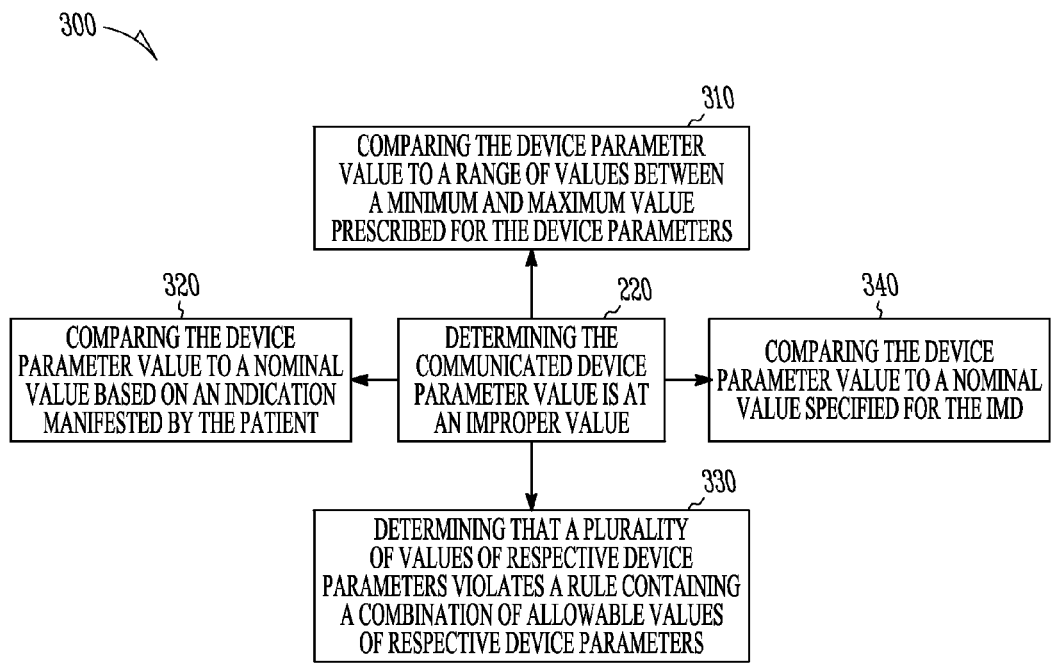
FIG. 3 illustrates an example of a method for determining that the communicated device parameter has an improper value.

FIG. 3 is a diagram 300 illustrating various examples for determining whether the communicated device parameter has an improper value.

At 310, determining whether the communicated device parameter has an improper value includes comparing the device parameter value to a range or list of allowable values, e.g., between a minimum and a maximum value prescribed for the device parameter, or to a list of allowable values.

At 320, determining whether the communicated device parameter value is at an improper value comprises comparing the device parameter value to a specified value corresponding to an indication manifested by the patient.

At 330, determining whether the communicated device parameter value is at an improper value includes determining that a plurality of values of respective device parameters violates a rule constraining a combination of allowable values of the respective device parameters.

At 340, determining whether the communicated device parameter value is at an improper value includes comparing the device parameter value to a nominal value specified for the IMD, e.g., without regard to a patient indication.

The external device can also use other techniques of determining whether one or more device parameter values communicated by the IMD is at an improper value.

Figure 4:
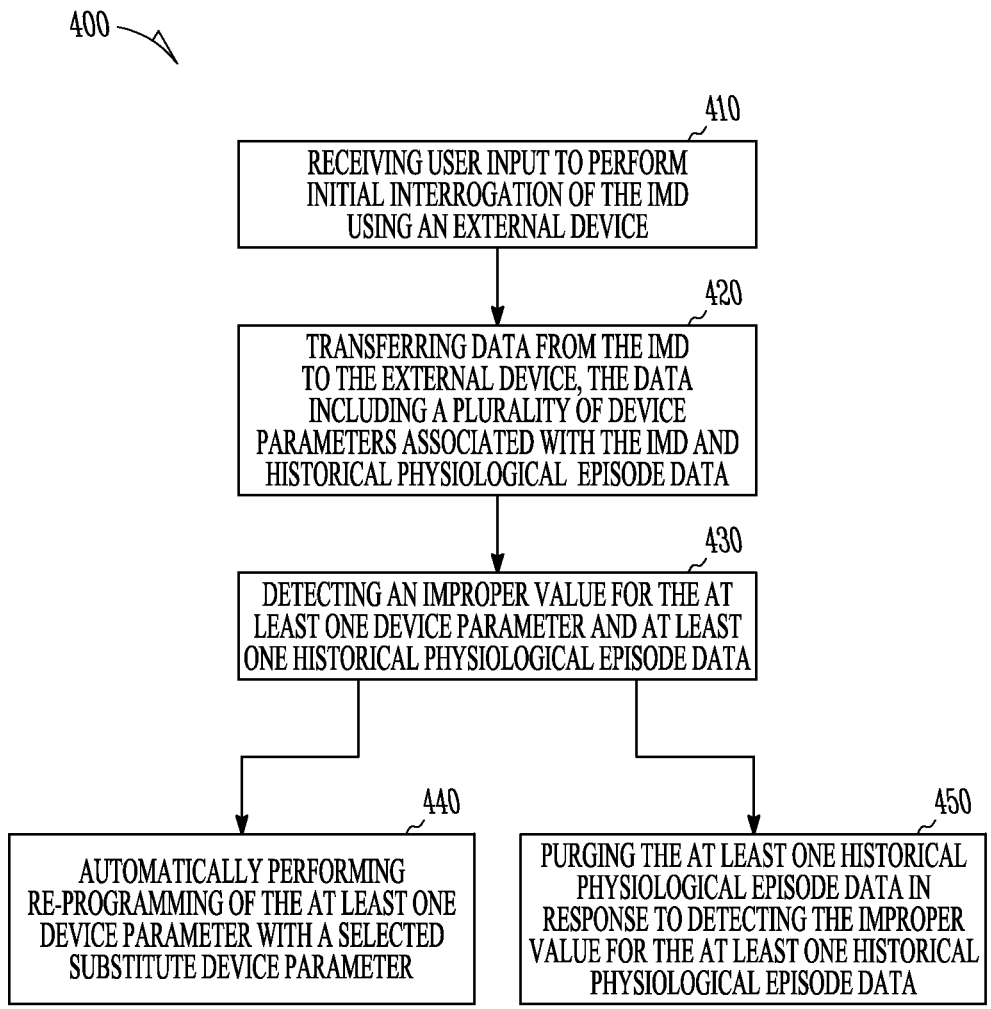
FIG. 4 illustrates another example of a method for handling data received from an implantable medical device.

FIG. 4 illustrates another example of a method 400 for handling data received from an implantable medical device for a patient.

At 410, the method 400 can include receiving user input initiating an initial interrogation of the IMD using an external device.

At 420, data can be transferred from the IMD to the external device, the data including a plurality of device parameters associated with the IMD and a plurality of historical physiological episode data associated with the patient.

At 430, method 400 can include detecting an improper value for at least one device parameter or at least one historical physiological episode data. Detecting at least one improper value of a device parameter can include determining whether a then-current device parameter value is improper, or it can include determining whether a logged device parameter value (e.g., that was stored in conjunction with a historical physiological episode and corresponding physiological data) is improper.

At 440, method 400 can include automatically re-programming the at least one device parameter with a selected substitute device parameter value in response to detecting the improper value for the at least one device parameter.

At 450, method 400 can includes ignoring or purging the at least one historical physiological episode data in response to detecting the improper value for (1) the at least one historical physiological episode data, or (2) detecting an improper logged device parameter value that was in effect during a time period when the historical physiological episode data was acquired.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A system comprising:
   a data processing device in communication with an implantable medical device (IMD) and configured to process a device control parameter value used in the IMD, wherein the device control parameter value is programmed in a device control parameter of the IMD to affect operation of the IMD, wherein the data processing device is configured to determine whether the device control parameter value is at an improper value, and wherein in response to a determination that the device control parameter value is at an improper value the data processing device is configured to:
      re-program the device control parameter of the IMD to replace the improper value with a substitute device control parameter value; and
      purge non-programmable measured data associated with the improper value.

2. The system of claim 1, comprising:
   the IMD, the IMD being configured for implanting in a patient.

3. The system of claim 1, comprising:
   a remote system, the remote system configured to communicate the substitute device control parameter value via a network to the data processing device.

4. The system of claim 1, wherein the data processing device is configured to compare the device control parameter value against an allowable range or list of values for the device control parameter.

5. The system of claim 1, wherein the data processing device is configured to determine that a plurality of values of respective device control parameters used in the IMD violates a rule constraining a combination of allowable values of the respective device control parameters.

6. The system of claim 5, wherein the data processing device is configured to re-program at least one of the plurality of values of respective device control parameters upon determining that the plurality of values of respective device control parameters violates the rule constraining the combination of allowable values of the respective device control parameters.

7. The system of claim 1, wherein the data processing device is configured to re-program the device control parameter to a nominal value, wherein the nominal value is specified for the IMD or is based on an indication manifested by the patient.

8. The system of claim 1, wherein the data processing device is configured to automatically disregard non-programmable measured data values used in the IMD associated with the improper value of the device control parameter.

9. The system of claim 1, wherein the data processing device is configured to automatically re-program the IMD device control parameter with a selected substitute device control parameter value in response to determining that the device control parameter value is at an improper value.

10. The system of claim 1, wherein the data processing device is configured to automatically disregard non-programmable measured data values and non-programmable physiological data values used in the IMD in response to determining that the device control parameter value is at an improper value.

11. A method of handling data used in an implantable medical device (IMD) for a patient, the method comprising:
   processing, at a data processing device, a parameter value of an IMD device control parameter used in the IMD, wherein the IMD device control parameter is programmed to affect operation of the IMD;
   determining, at the data processing device, that the parameter value is an improper value;
   in response to determining that the parameter value is an improper value, performing at least one of:
      re-programming the IMD device control parameter replace the improper value with a selected substitute device control parameter value;
      purging, from the IMD, the non-programmable measured data associated with the improper value; or
      disregarding, at the data processing device, at leas one non-programmable measured data value originating from the IMD.

12. The method of claim 11, wherein determining that the parameter value is at an improper value includes comparing the communicated device control parameter value against an allowable range or list of values for the IMD device control parameter.

13. The method of claim 11, wherein determining that the parameter value is at an improper value includes determining that a plurality of values of respective IMD device control parameters used in the IMD violates a rule constraining a combination of allowable values of the respective IMD device control parameters, and wherein the method further comprises re-programming at least one of the plurality of values of respective IMD device control upon determination that the plurality of values of respective IMD device control parameters violates the rule constraining the combination of allowable values of the respective IMD device control parameters.

14. The method of claim 11, wherein re-programming the IMD device control parameter includes re-programming the IMD device control parameter to a nominal value specified for the IMD or to a nominal value based on an indication manifested by the patient.

15. The method of claim 11, wherein purging the non-programmable measured data includes purging physiological data associated with the improper value.

16. The method of claim 11, comprising, in response to the determining that the parameter value is at an improper value, transmitting commands for automatically re-programming the IMD device control parameter on the IMD with a selected substitute device control parameter value.

17. The method of claim 11, comprising, in response to the determining that the parameter value is at an improper value, transmuting commands for automatically purging the non-programmable measured data from the IMD.

18. The method of claim 11, wherein re-programming the IMD device control parameter includes re-programming at least one of a therapy parameter or a sensing parameter, wherein the therapy parameter includes a bradycardia mode parameter, a tachycardia mode parameter, or pacing rate parameter.

19. The method of claim 11, wherein purging the non-programmable measured data includes purging at least one of episode identification data, episode detail data, episode therapy data, electro-gram data, episode marker data, or a trended data, wherein the trended data includes at least one of heart rate data, activity level data, fault data, pace count data, sense count data, or therapy count data.

20. The method of claim 11, comprising communicating an alert to a user upon determining, at the device, that the IMD device control parameter is at an improper value.

21. A non-transitory device-readable medium comprising device-readable instructions that, when performed by a data processing device, cause the data processing device to:
   process a value of an control parameter used in an implantable medical device (IMD), wherein the control parameter affects operation of the IMD;
   determine whether the value is not within an allowable range or list of values;
   in response to determining that the value is not within an allowable range or list of values, conducting operations to automatically:
      obtain a replacement value for the control parameter;
      re-program the IMD to replace the value with the replacement value; and remove non-programmable data from the IMD associated with the control parameter.

* * * * *